United States Patent
Shah et al.

(12) 
(10) Patent No.: US 11,460,400 B2
(45) Date of Patent: Oct. 4, 2022

(54) USE OF IR SPECTROSCOPY TO EVALUATE PENETRATION OF REAGENTS INTO BIOLOGICAL SPECIMEN

(71) Applicant: Sakura Finetek U.S.A., Inc., Torrance, CA (US)

(72) Inventors: Amit D. Shah, Redondo Beach, CA (US); Cristina R. Flores, Downey, CA (US)

(73) Assignee: SAKURA FINETEK U.S.A., INC., Torrance, CA (US)

(*) Notice: Subject to any disclaimer, the term of this patent is extended or adjusted under 35 U.S.C. 154(b) by 183 days.

(21) Appl. No.: 16/923,056

(22) Filed: Jul. 7, 2020

(65) Prior Publication Data

US 2022/0011227 A1   Jan. 13, 2022

(51) Int. Cl.
*G01N 21/55* (2014.01)
*G01N 21/552* (2014.01)
(Continued)

(52) U.S. Cl.
CPC .......... *G01N 21/552* (2013.01); *G01N 21/35* (2013.01); *G01N 33/4833* (2013.01)

(58) Field of Classification Search
CPC .. G01N 21/552; G01N 21/35; G01N 33/4833; G01N 21/3563
See application file for complete search history.

(56) References Cited

U.S. PATENT DOCUMENTS

| | | | |
|---|---|---|---|
| 3,370,502 A * | 2/1968 | Wilks, Jr. ............. | G01N 21/552 250/343 |
| 3,902,807 A * | 9/1975 | Fleming ............... | G01N 21/552 250/343 |

(Continued)

FOREIGN PATENT DOCUMENTS

| | | | |
|---|---|---|---|
| JP | 6676160 B2 * | 4/2020 | ............... G01N 1/30 |
| JP | 6676160 B2 | 4/2020 | |

(Continued)

OTHER PUBLICATIONS ip.com Search (Year: 2022).*
Sakura Finetek U.S.A. Inc., Related Application, PCT Int'l Patent Application No. PCT/US2021/024480, International Search Report and the Written Opinion, dated Aug. 18, 2021.
(Continued)

*Primary Examiner* — Roy M Punnoose
(74) *Attorney, Agent, or Firm* — William Thomas Babbitt, Esq.; Leech Tishman Fuscaldo & Lampl

(57) ABSTRACT

Apparatuses for measuring sample materials (such as tissue samples) and associated methodologies and instrumentation involve a spectroscopy system or device configured with a sample measuring device (e.g., an attenuated total reflection infrared (ATR-IR) sample measuring device) including a crystal defining a sample receiving surface/interface operatively connected to an IR source and an IR detector. The sample receiving surface/interface facilitates assessing presence (and optionally, amount) of a fixative (e.g., formaldehyde) in sample materials, tissue samples for example. Measurements are taken at one or multiple locations within a sample placement structure/area, which can be provided in the form of a probe or a raised piercing structure containing one or more ATR-IR (or other) sample measuring devices. The probe can include a piercing structure or mechanism at a distal (open) end of the probe configured to create a passage to a selected location (depth) within the sample material in a minimally invasive manner so that the sample is not severely damaged during testing.

22 Claims, 8 Drawing Sheets

(51) Int. Cl.
*G01N 21/35* (2014.01)
*G01N 33/483* (2006.01)

(56) References Cited

U.S. PATENT DOCUMENTS

| | | | | |
|---|---|---|---|---|
| 4,835,389 | A * | 5/1989 | Doyle | G01N 21/552 |
| | | | | 250/343 |
| 5,051,551 | A * | 9/1991 | Doyle | G01N 21/552 |
| | | | | 250/341.8 |
| 5,170,056 | A * | 12/1992 | Berard | G01N 21/8507 |
| | | | | 250/341.8 |
| 5,703,366 | A * | 12/1997 | Sting | G01N 21/552 |
| | | | | 250/341.8 |
| 5,945,674 | A | 8/1999 | Dukor | |
| 6,137,108 | A * | 10/2000 | DeThomas | G01J 3/42 |
| | | | | 356/342 |
| 6,818,892 | B1 * | 11/2004 | Etienne | G01J 5/34 |
| | | | | 250/338.3 |
| 7,339,657 | B2 * | 3/2008 | Coates | G01N 33/2888 |
| | | | | 356/417 |
| 7,860,355 | B2 * | 12/2010 | Mikkelsen | G01N 21/552 |
| | | | | 385/12 |
| 7,993,927 | B2 | 8/2011 | Frangioni | |
| 9,366,601 | B1 * | 6/2016 | Chen | G01N 1/00 |
| 9,383,306 | B2 * | 7/2016 | Koerner | G01B 9/02091 |
| 10,013,760 | B2 | 7/2018 | Bhargava | |
| 10,267,769 | B2 | 4/2019 | Otter et al. | |
| 2002/0060020 | A1 * | 5/2002 | Irwin | G01N 21/552 |
| | | | | 162/50 |
| 2003/0176775 | A1 * | 9/2003 | Berman | G01N 21/15 |
| | | | | 600/310 |
| 2003/0179368 | A1 * | 9/2003 | Li | G01N 21/94 |
| | | | | 438/16 |
| 2006/0043301 | A1 * | 3/2006 | Mantele | G01N 21/552 |
| | | | | 250/339.11 |
| 2012/0035583 | A1 * | 2/2012 | Sepkuty | A61B 5/6849 |
| | | | | 607/113 |
| 2013/0037719 | A1 * | 2/2013 | Melling | G01N 21/85 |
| | | | | 250/340 |
| 2013/0224791 | A1 | 8/2013 | Taft et al. | |
| 2015/0110381 | A1 | 4/2015 | Parvin et al. | |
| 2016/0139047 | A1 | 5/2016 | Geiger et al. | |
| 2016/0143539 | A1 * | 5/2016 | Koerner | A61B 5/0086 |
| | | | | 600/475 |
| 2016/0235303 | A1 | 8/2016 | Fleming et al. | |
| 2016/0313224 | A1 | 10/2016 | Lau et al. | |
| 2017/0122872 | A1 | 5/2017 | Sood et al. | |
| 2017/0148164 | A1 | 5/2017 | Totsu et al. | |
| 2017/0284859 | A1 | 10/2017 | Bauer et al. | |
| 2017/0284920 | A1 | 10/2017 | Bauer et al. | |
| 2017/0336363 | A1 | 11/2017 | Bauer et al. | |
| 2018/0238897 | A1 | 8/2018 | Martinic et al. | |
| 2018/0306726 | A1 * | 10/2018 | Mann | G01N 21/552 |
| 2018/0313792 | A1 | 11/2018 | Cook | |
| 2019/0110687 | A1 | 4/2019 | Coe et al. | |
| 2019/0196163 | A1 | 6/2019 | Kim et al. | |
| 2019/0234869 | A1 | 8/2019 | Sajjadi et al. | |
| 2019/0277755 | A1 * | 9/2019 | Cohen | G01N 1/286 |
| 2019/0293525 | A1 | 9/2019 | Bauer et al. | |
| 2019/0302020 | A1 | 10/2019 | Dodson | |
| 2019/0369017 | A1 * | 12/2019 | Bauer | G01N 1/30 |

FOREIGN PATENT DOCUMENTS

| | | | | |
|---|---|---|---|---|
| WO | WO-0169208 | A1 * | 9/2001 | G01N 21/35 |
| WO | WO-03083458 | A2 * | 10/2003 | G01N 21/05 |
| WO | 2019/150408 | A1 | 8/2019 | |

OTHER PUBLICATIONS

Gentner J.M. et al: "Natural History Specimen Analysis Using Micro FT-IR Attenuated Total Reflectance Spectroscopy and Transmission Electron Microscopy" Spectrochimica Acta Part A: Molecular and Biomolecular Spectroscopy, Elsevier, Amsterdam, NL. vol. 55, Sep. 20, 1999.

Madhavan K. et al: "Evaluation of composition and crosslinking effects on collagen-based composite constructs", Acta Biomaterialia, Elsevier, Amsterdam, NL, vol. 6, No. 4, Apr. 2010.

\* cited by examiner

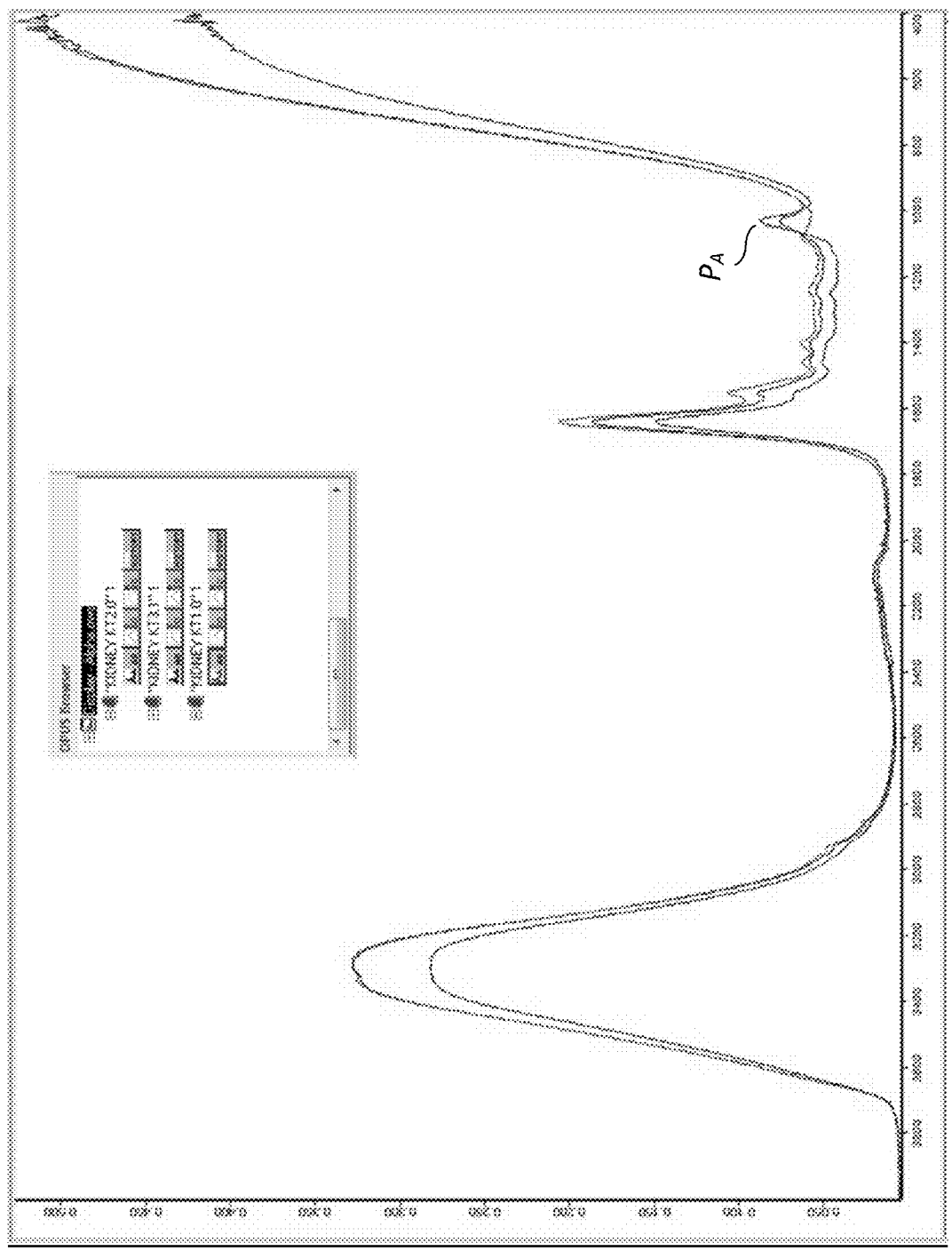

USE OF IR SPECTROSCOPY TO EVALUATE PENETRATION OF REAGENTS INTO BIOLOGICAL SPECIMEN

TECHNICAL FIELD

Various embodiments of the present invention generally relate to tissue processing, in particular, technologies, instrumentation and methods utilizing IR spectroscopy to assess presence of a fixative substance (e.g., formalin) within a tissue sample.

INTRODUCTION

Tissues from the body taken for diagnosis of disease processes are often processed in the histology laboratory to produce thin tissue sections which can be mounted on tissue slides, stained, and viewed under a microscope by a pathologist for analysis. These pre-analytical processes generally include, in order, gross examination fixation, dehydration, clearing, paraffin infiltration and embedding. The procedure is used for processing tissues including biopsies, larger specimens removed at surgery, or tissues from autopsy.

Gross examination generally consists of describing the macroscopic specimen and placing all or selected parts of it into a small plastic cassette which holds the tissue while it is being processed to a paraffin block. Initially, the cassettes are placed into a fixative.

Following gross examination, a tissue is fixated. A purpose of fixation is to preserve tissues permanently in as life-like a state as possible by altering structures of proteins such that degradation by autolysis does not occur. A variety of fixatives are available for use, depending on the type of tissue present and features to be demonstrated. Major groups of fixatives, classified according to mechanism of action include aldehydes, mercurials, alcohols, oxidizing agents and picrates. Formalin is an aqueous solution of formaldehyde (gas). Actual fixation takes place by formaldehyde. Formalin fixation is best carried around neutral pH, for example, in the range of 6-8. Hypoxia of tissues tends to lower the pH, so there should be buffering capacity in the fixative to prevent excessive acidity. Common buffers include phosphate, bicarbonate, malate, cacodylate, and veronal. Commercial formalin, for example, may be buffered with phosphate at a pH of 7. Penetration of tissues depends upon the diffusability of each individual fixative. One way to improve penetration of a fixative is to gross (cut) the tissue thinly (2 to 3 millimeters (mm)). Penetration into a thin tissue section will occur more rapidly than for a thick section. The volume of fixative is generally important with a 10:1 ratio or greater of fixative to tissue typically targeted. Agitation of the specimen in a fixative will often also enhance fixation.

Once the tissue has been fixed or fixated, the tissue needs to be processed into a form in which it can be made into thin sections for microscopic examination. The usual way this is done is with paraffin. Tissues embedded in paraffin, which provides a solid support matrix for the tissue, allowing it be sectioned at a thickness on the order of 2 to 20 microns. Getting fixed tissue into paraffin for sectioning is called tissue processing with the main steps in this process being dehydration, clearing, infiltration and embedding.

Tissues fixed in aqueous solutions cannot be directly infiltrated with paraffin. First, the water from the tissues must be removed by dehydration. This may be done with a series of alcohols at different concentrations (e.g., 70 percent to 95 percent to 100 percent). Alternatively, the dehydration is done with a mixture of formalin and alcohol. Other dehydrants can also be used such as acetone or mixtures of different solvents.

Following dehydration, the tissue is cleared. "Clearing" consists of removal of the dehydrant and some of the lipids with a substance that will be miscible with the embedding medium (e.g., paraffin). The most common clearing agent is xylene.

Once cleared, the tissue is infiltrated with an embedding agent such as paraffin. Finally, the tissue in a cassette or removed from its cassette is placed into molten paraffin and then the paraffin is cooled to form a solidified block embedding or encapsulating the tissue so that it can be sectioned. Alternatively, the tissue can be processed in a sectionable cassette, embedded in paraffin along with the cassette and sectioned. Once the tissue has been embedded in a solid paraffin block, the tissue can be cut into sections that can be placed on a slide. This is done with a microtome. Once sections are cut, they are floated on a warm water bath that helps remove any wrinkles. The tissue sections in paraffin are then picked up from the water bath and placed on a glass microscope slide.

Further with regard to fixation, it would be helpful to be able to evaluate penetration of fixative (e.g., the formaldehyde present in formalin) in a tissue sample in a manner that would help provide an understanding of the extent of tissue fixation to determine if the tissue is ready for processing.

It would be helpful to be able to assess presence of a fixative substance (e.g., the formaldehyde present in formalin) within tissue samples that are thicker and/or larger in size (area).

It would be helpful to be able to configure or provide an IR spectroscopy system/device with a tissue sample measuring device capable of and which facilitates obtaining measurement data indicating whether there is presence of a fixative substance (e.g., the formaldehyde present in formalin) at a selected depth location within a tissue sample.

It would be helpful to be able to configure or provide an IR spectroscopy system/device with tissue sample measuring instrumentatition for simultaneously obtaining measurement data indicating whether there is presence of a fixative substance (e.g., the formaldehyde present in formalin) at multiple different locations of (and at respective selected depths within) a tissue sample.

BRIEF DESCRIPTION OF THE DRAWINGS

FIG. 1A shows plots of IR spectra (Absorbance vs Wavenumber [cm-1]) for kidney tissue measured at different times during infiltration of formalin/formaldehyde into the kidney tissue;

DESCRIPTION

Various embodiments of the invention involve configuring and/or utilizing an attenuated total reflection infrared (ATR-IR) sample measuring device including a crystal defining a sample receiving surface/interface to assess (and optionally, quantify) presence of a fixative (e.g., the formaldehyde present in formalin), for example, in samples from tissue undergoing fixative (e.g., formalin) infiltration. In example embodiments, the sample receiving surface/interface is provided in the form of, or contained within, a probe or other structure suitable for advancing (pushing or otherwise repositioning) the sample receiving surface/interface to a selected location (or depth) within the sample material. In example embodiments, the probe includes a piercing structure or mechanism at a distal (open) end of the probe configured to create a passage to a selected location (depth) within the sample material in a minimally invasive manner so that the sample material is not severely damaged during testing. Example embodiments and implementations involve instrumentation configured or provided to facilitate such assessments at multiple different locations within a sample placement structure/area of a measuring instrument for simultaneously measuring at the different locations.

Figure 2:
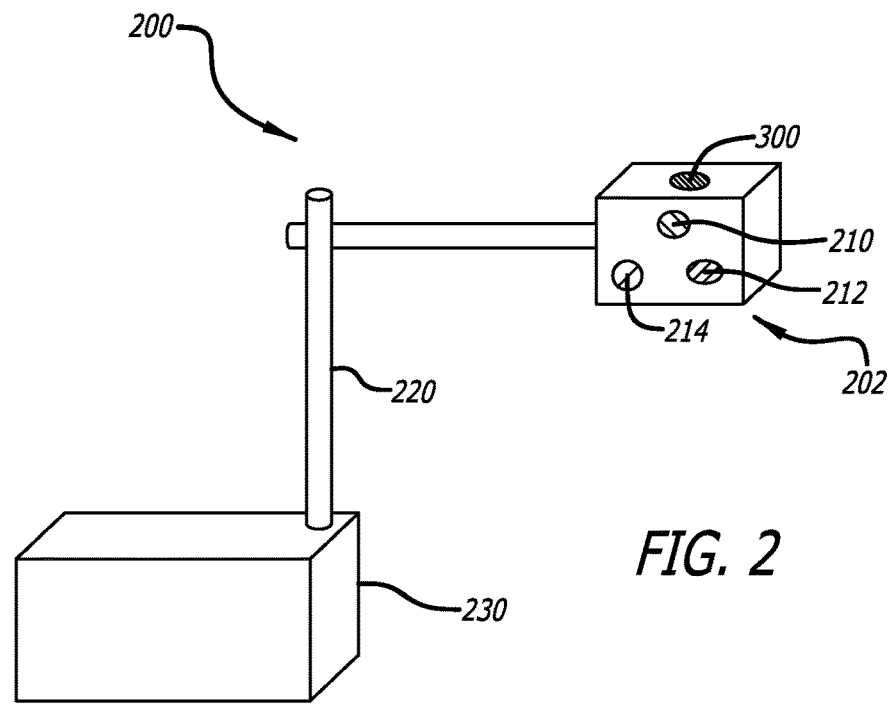
FIG. 2 shows an example embodiment of a spectrometry system for evaluating samples from tissue undergoing formalin infiltration.

With reference to FIG. 2, in this example embodiment, a spectrometry system 200 is provided/configured for evaluating samples from tissue undergoing formalin infiltration. The spectrometry system 200 includes an IR spectrometer 202 which can be supported by a stand 220 to place in grossing station (optional) and a base plate 230 which can include computer/processor components (optional) supporting the stand 220. The spectrometry system 200 includes a sample placement structure 300 (surface upon which a tissue sample is placed) and several indicators which can be processor controlled lights or other human and/or machine perceivable phenomena inclusive of in this example system: an analysis status indicator 210 (e.g., complete/onging), an insufficient presence of fixative indicator 212 (e.g., not enough formaldehyde detected) and a sufficient presence of fixative indicator 214 (e.g., formaldehyde detected).

Figure 1B:
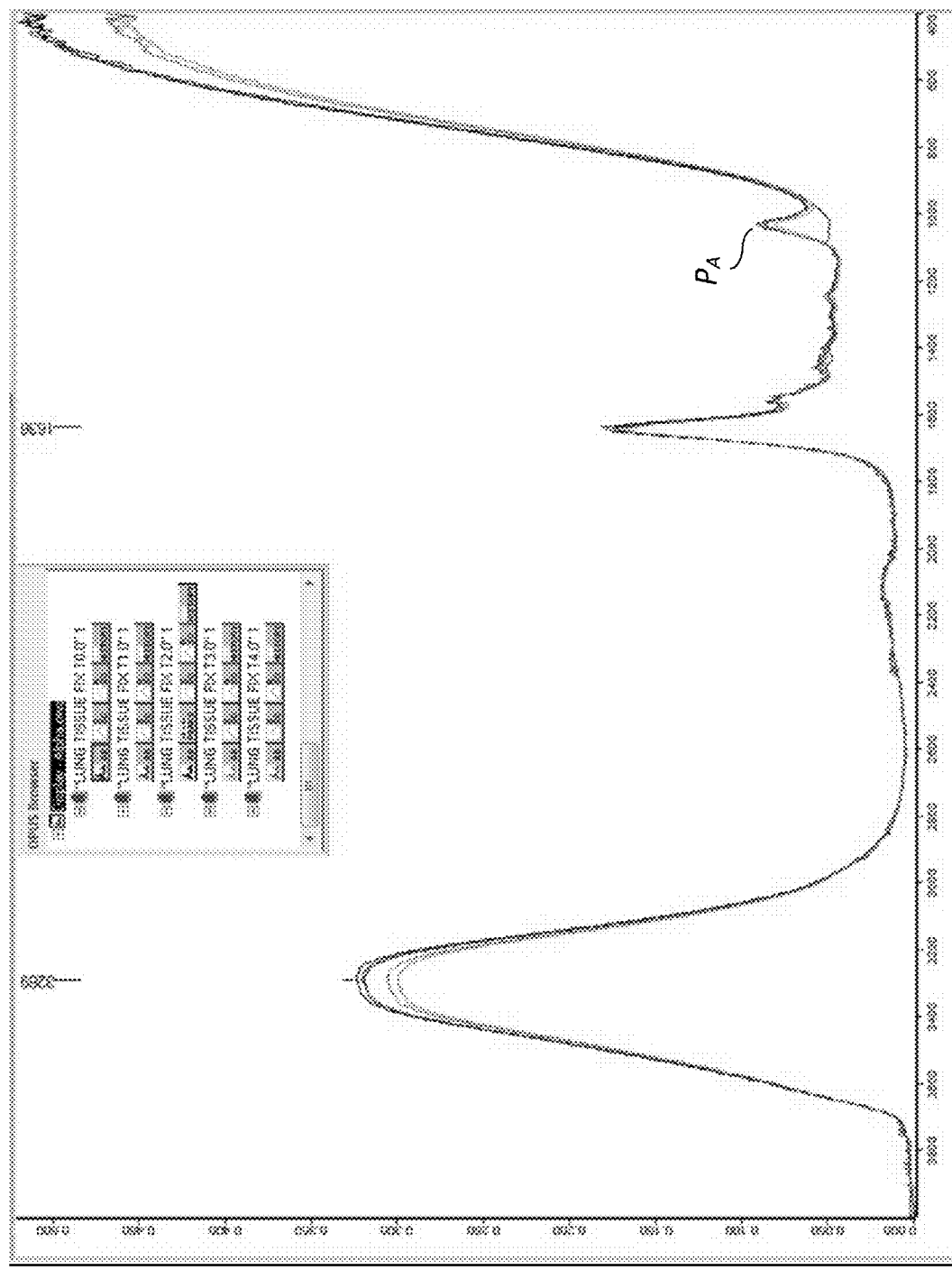
FIG. 1B shows plots of IR spectra (Absorbance vs Wavenumber [cm-1]) for lung tissue measured at different times during infiltration of formalin/formaldehyde into the lung tissue.

With reference also to FIGS. 1A and 1B, in operation, the spectrometry system 200 (which can be configured to utilize one or more of IR, FTIR and ATR-IR spectroscopy technology) facilitates the testing of tissue samples to determine whether the fixative chemicals have adequately penetrated (to an inside location of, or specified location within) the tissue. In example embodiments and implementations, IR spectroscopy is utilized to provide an information of presence of formaldehyde indicated by C=O stretch. The inventors tested several animal tissues—FIGS. 1A and 1B, first checking their IR spectra before fixation (that is, prior to commencing fixative infiltration), and periodically during fixation (that is, during fixative infiltration) in 10% neutral buffered formalin (NBF) solution, which is typically a solution of approx. 3.7% formaldehyde $CH_2O$ in 95-97% water $H_2O$ with a small amount of buffer salts included). It was observed that a new stretch appeared having an absorbance peak (denoted PA in FIGS. 1A and 1B) at approximately between 1000 $cm^{-1}$ and 1100 $cm^{-1}$ that grew stronger every hour indicating the presence of formalin in the tissue. Presence of methylene linkages in spectra can also be used to assess fixation. By way of example, an instrument used for testing the tissues includes (or is provided or configured with) a sample placement surface that has a sample receiving surface/interface defined by an ATR-IR diamond, where tissue samples to be tested are placed—after they are washed if needed to remove fixative solution.

In one testing methodology, the tissue samples undergoing fixation are bisected or cut to expose their deepest or hardest to reach areas or to expose the surface to be tested. A clean knife is used to expose area of interest without contaminating it. If needed, the exposed area can be washed with water and excess water soaked up using a paper towel or an absorbant material. The tissue area of interest is then placed on the ATR-IR crystal/diamond and analysis is performed. Software (e.g., an executable computer program) is configured/programmed in a manner, utilizing generalized programming techniques and practices understood by those of skill in the art, facilitating the processing of IR spectra (data) to identify presence and intensity of the specific IR stretch of interest and provide indication of go/no-go by green/red light or pass/fail etc. Presence of the stretch could mean presence of formaldehyde or new bonds formed; therefore even if the fixation is not complete, it has been observed (and in some circumstances can be assumed) that during processing temperatures and exposure the tissues will behave as adequately fixed tissues.

Figures 3A, 3B, 3C:
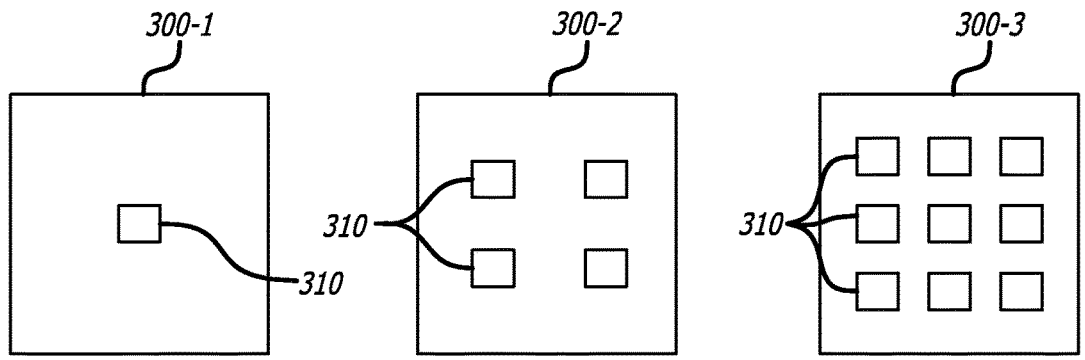
FIG. 3A shows an example embodiment of a sample placement structure (surface upon which tissue sample is placed) that has a single sample receiving surface/interface defined by a crystal of a sample measuring device.
FIG. 3B shows another example embodiment of a sample placement structure (surface upon which tissue sample is placed) that has a four (4) distinct spatially separated sample receiving surfaces/interfaces, each sample receiving surface/interface being defined by a crystal of a sample measuring device.
FIG. 3C shows another example embodiment of a sample placement structure (surface upon which tissue sample is placed) that has a nine (9) distinct spatially separated sample receiving surfaces/interfaces, each sample receiving surface/interface being defined by a crystal of a sample measuring device.

FIG. 3A depicts an example of a sample placement structure/area, namely, a sample placement structure 300-1 (e.g., a surface upon which a tissue sample to be measured is placed) with a (single) sample measuring device 310 that has a sample receiving surface/interface defined by a crystal such as for example an ATR-IR diamond. Crystal materials other than diamond, germanium (Ge) ATR crystal for example, can be utilized in some tissue sample measuring device configurations. In example embodiments and implementations, the sample receiving surface/interface is part of and defined by a crystal of an ATR-IR sample measuring device.

Figure 4:
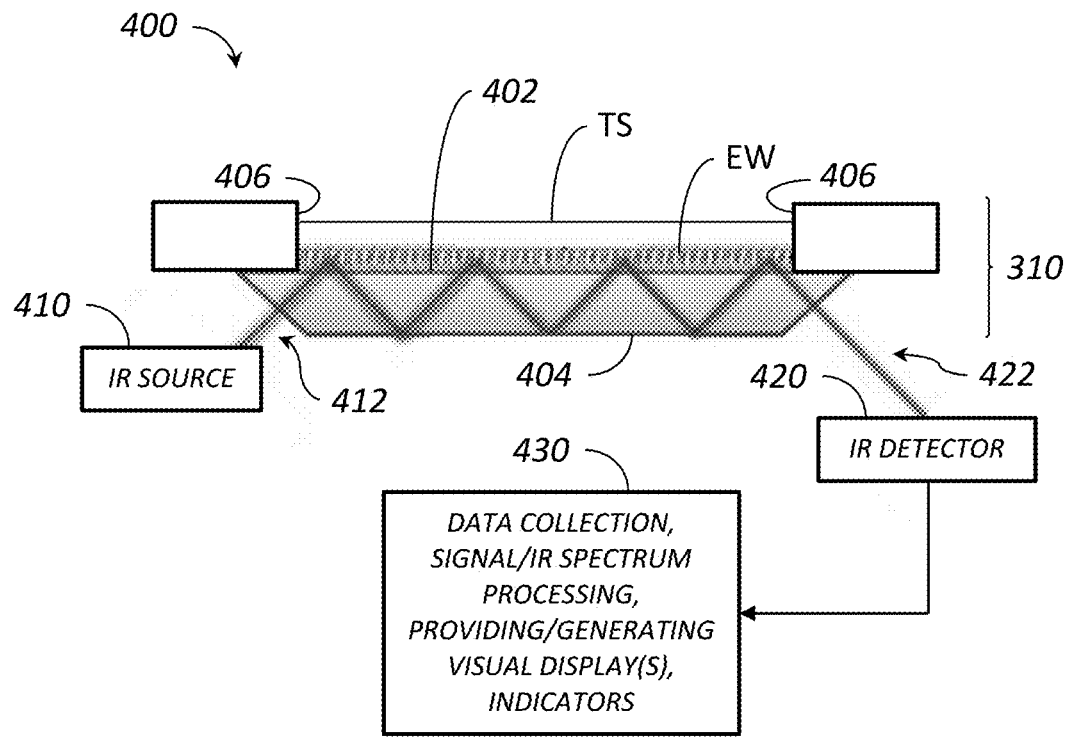
FIG. 4 shows an example embodiment of a spectrometry system for evaluating samples from tissue undergoing formalin infiltration, the system being provided in the form of an attenuated total reflection infrared (ATR-IR) sample measuring device including a crystal defining a sample receiving surface/interface.

FIG. 4 shows an example embodiment of a spectrometry system 400 for evaluating sample materials (e.g., samples from tissue undergoing formalin infiltration), the system 400 including a sample measuring device 310 (e.g., provided in the form of an ATR-IR sample measuring device) including a sample receiving surface/interface 402 defined by a crystal 404 and located within periphery boundary 406, the sample receiving surface/interface 402 being operatively connected via associated optics 412, 422 (at opposite ends of the crystal 404) to an IR source 410 and an IR detector 420, respectively. Other couplings of the crystal 404 with the IR source 410 and the IR detector 420 are also contemplated. In operation, a tissue sample (denoted TS) is placed on the sample receiving surface/interface 402. The internal reflectance of the crystal 404 creates an evanescent wave (denoted EW) that extends beyond the sample receiving surface/interface 402 of the crystal into the sample (held) in contact with the crystal. Presence of formaldehyde or new bonds formed in the fixative infiltrated tissue contribute to infrared absorption, and the attenuated energy from each evanescent wave is passed back to the IR beam. The sample receiving surface/interface 402 can be provided/defined by a single or multiple reflection ATR element as appropriate for a particular measuring device, application requirements and sample materials (e.g., tissue sample) properties. Accordingly, it is to be understood that the illustration in FIG. 4 of the sample measuring device 310 as including a multiple reflection ATR element and the description herein additionally provide explicit support for embodiments in which the sample measuring device 310 includes a single reflection ATR element. In this example embodiment, the spectrometry system 400 includes data collection, spectra analysis and user interface components 430 operatively coupled or interfaced with the IR detector 420. The spectrometry system 400 can be configured to perform both qualitative and quantitative analysis. Quantitatively: the software can be configured/programmed to facilitate providing an indication of level/amount/extent of formalin present which can also be further used to determine fixation. One approach to achieve this is by determining series of various concentration of fixative present in tissue vs absorbance and then using that data to estimate concentration of fixative in the test sample. The data collection, spectra analysis and user interface components 430 can include user interfaces (e.g., one or more display screen, touch-screen or remote display/monitor) and a computer, server or the like configured with software programmed to facilitate data collection, detector output signal/IR spectrum processing, application programming (and other) interfaces as required, and providing/generating visual display(s), indicators and other outputs such as described herein. By way of example, Fourier transform infrared (FTIR) spectroscopy methodologies are utilized to convert the output of the IR detector 420 to interpretable spectra patterns (such as shown for example in FIGS. 1A and 1B). The data collection, spectra analysis and user interface components 430 can include data storage devices (e.g., on the instrument) for record keeping and providing access to control libraries and other data resources. Alternatively or additionally, the data collection, spectra analysis and user interface components 430 can be configured to facilitate transfer and remote storage of collected data as well as access to networks and external data and software resources and control inputs.

The sample measuring device 310 inclusive of its sample receiving surface/interface 402 can be provided in the form of, or contained within, a probe (e.g., a tissue probe) or other tool, implement or structure suitable for advancing (pushing or otherwise repositioning) the sample receiving surface/interface to a selected location (or depth) within the sample material (e.g., a tissue sample).

Figure 5:
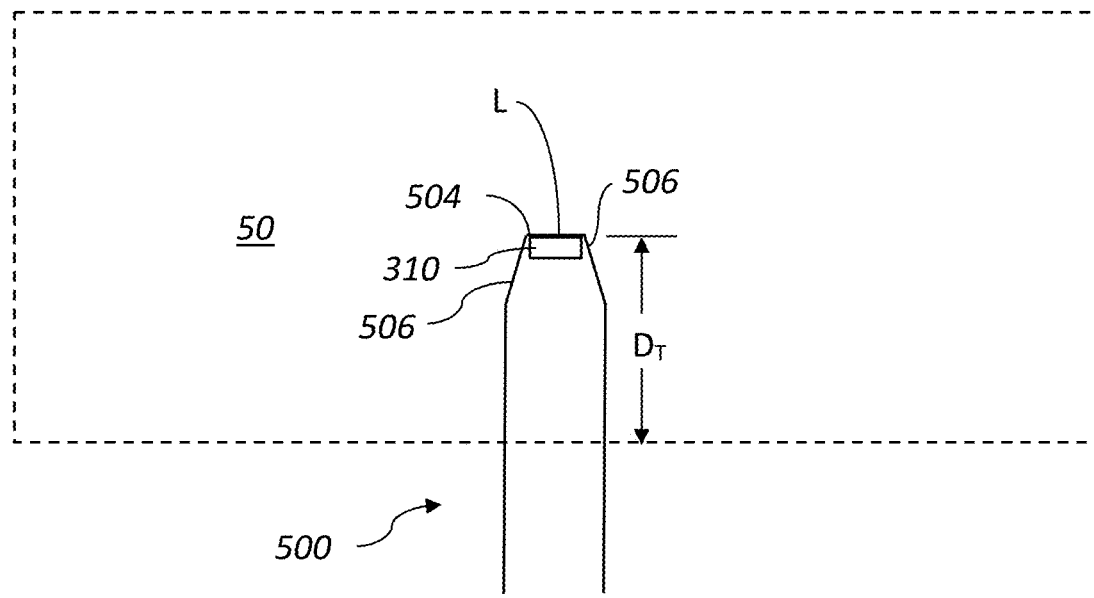
FIG. 5 shows an example embodiment of a tissue probe configured with an attenuated total reflection infrared (ATR-IR) sample measuring device including a crystal defining a sample receiving surface/interface which has been advanced (pushed) into a tissue sample bringing a tissue (surface or mass) at a selected depth location (denoted "L") within the tissue sample directly into contact with the sample receiving surface/interface.

FIG. 5 shows an example embodiment of a sample probe 500 (e.g., a tissue probe) configured with a sample measuring device 310, e.g., an attenuated total reflection infrared (ATR-IR) sample measuring device including a crystal defining a sample receiving surface/interface such as previously described in relation to FIG. 4. The sample probe 500 includes a distal open end 504 adjacent to which the sample measuring device 310 is located with its a sample receiving surface/interface distally directed (i.e., positioned and oriented in relation to the distal open end 504 to accommodate sample material advancing through the distal open end to be placed (pressed against) sample receiving surface/interface. In this illustration, the probe 500 is shown advanced (pushed) into a sample material 50 (e.g., a tissue sample) bringing material (e.g., a tissue surface or mass) at a selected depth location (denoted "L") directly into contact with the sample receiving surface/interface. The sample probe 500 includes surfaces/edges 506 which in this example embodiment taper inward moving distally along the probe toward the open end 504. The surfaces/edges 506 can be provided in various forms, generally for purposes of this description falling into the categories of non-sharp and sharp (or piercing). In an embodiment where the surfaces/edges 506 are non-sharp, the probe 500 can serve as a measuring wand or a measuring device suitable for being (non-destructively) advanced into already formed openings, channels and the like. In an embodiment where the surfaces/edges 506 are sharps (e.g., cutting edges), the probe 500 allows a user to cut (slice or bore) a path through the sample material to a selected depth location therein. Accordingly, it should be understood that the probe 500 can be variously configured (e.g., with changeable/replaceable exterior enclosures) to measure sample materials at a top surface or an exposed surface (e.g., created by grossing) of a sample material, as well as at a selected depth location within the sample when the probe is configured as a sharp or cutting device. It should also be understood that the surfaces/edges described herein can be provided as sharps (e.g., cutting edges) of various shapes including but not limited to straight, curved and circular cutting edges.

In example embodiments, the sample probe (e.g., a tissue probe) includes a piercing structure and/or cutter at a distal (open) end of the probe configured to create a passage to a selected location (depth) within the sample material (e.g., tissue) in a minimally invasive manner so that the sample material is not severely damaged during testing.

Figure 6A:
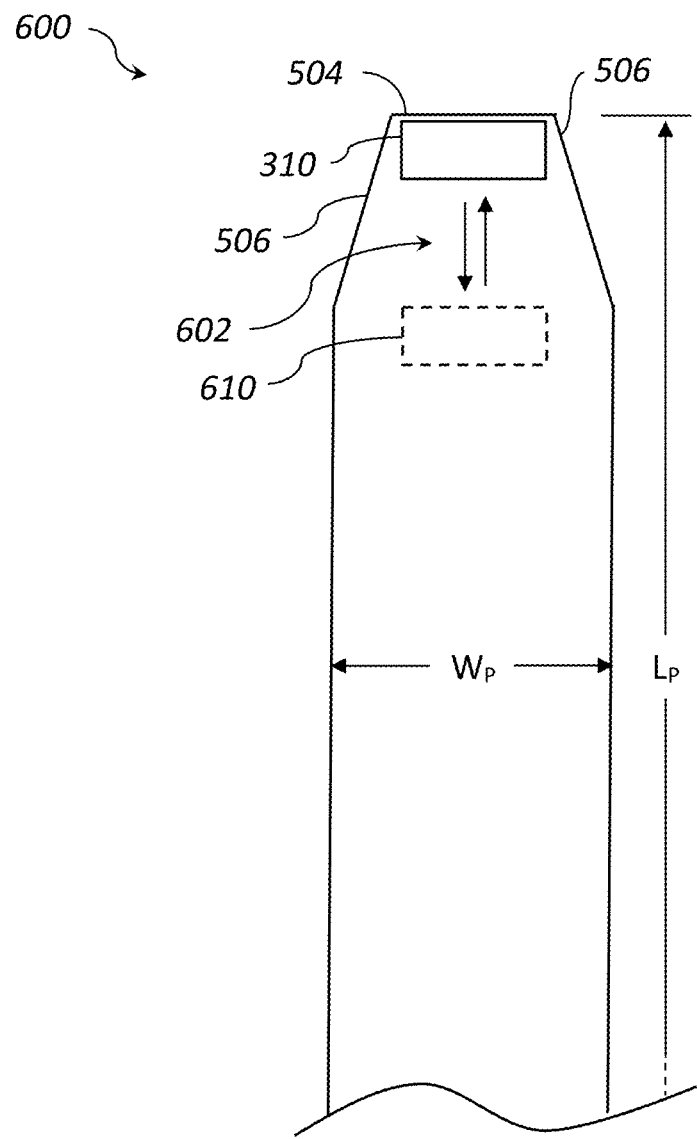
FIG. 6A shows another example embodiment of a tissue probe which includes a piercing structure at a distal open end of probe; the tissue probe including a sample receiving surface/interface configured to be repositionable between a forward/extended position adjacent the distal end (of the probe) and a rearward/retracted position recessed within the probe enclosure away from the distal open end.

FIG. 6A shows another example embodiment of a sample probe 600 (e.g., a tissue probe) configured with a sample measuring device 310, e.g., an attenuated total reflection infrared (ATR-IR) sample measuring device including a crystal defining a sample receiving surface/interface such as previously described in relation to FIG. 4. The sample probe 500 includes a distal open end 504 adjacent to which the sample measuring device 310 is located with its a sample receiving surface/interface distally directed (i.e., positioned and oriented in relation to the distal open end 504 to accommodate sample material advancing through the distal open end to be placed (pressed) against sample receiving surface/interface. In this example embodiment, the probe 600 includes surfaces/edges 506 configured (shaped) to provide a piercing structure at a distal open end of probe; and the sample measuring device 310 is configured to be repositionable (as denoted by the bi-directional arrows 602) between a forward/extended position adjacent the distal end (of the probe) and a rearward/retracted position 610 (shown in dashed lines) recessed within the probe enclosure away from the distal open end 504 (e.g., as shown).

Figure 6B:
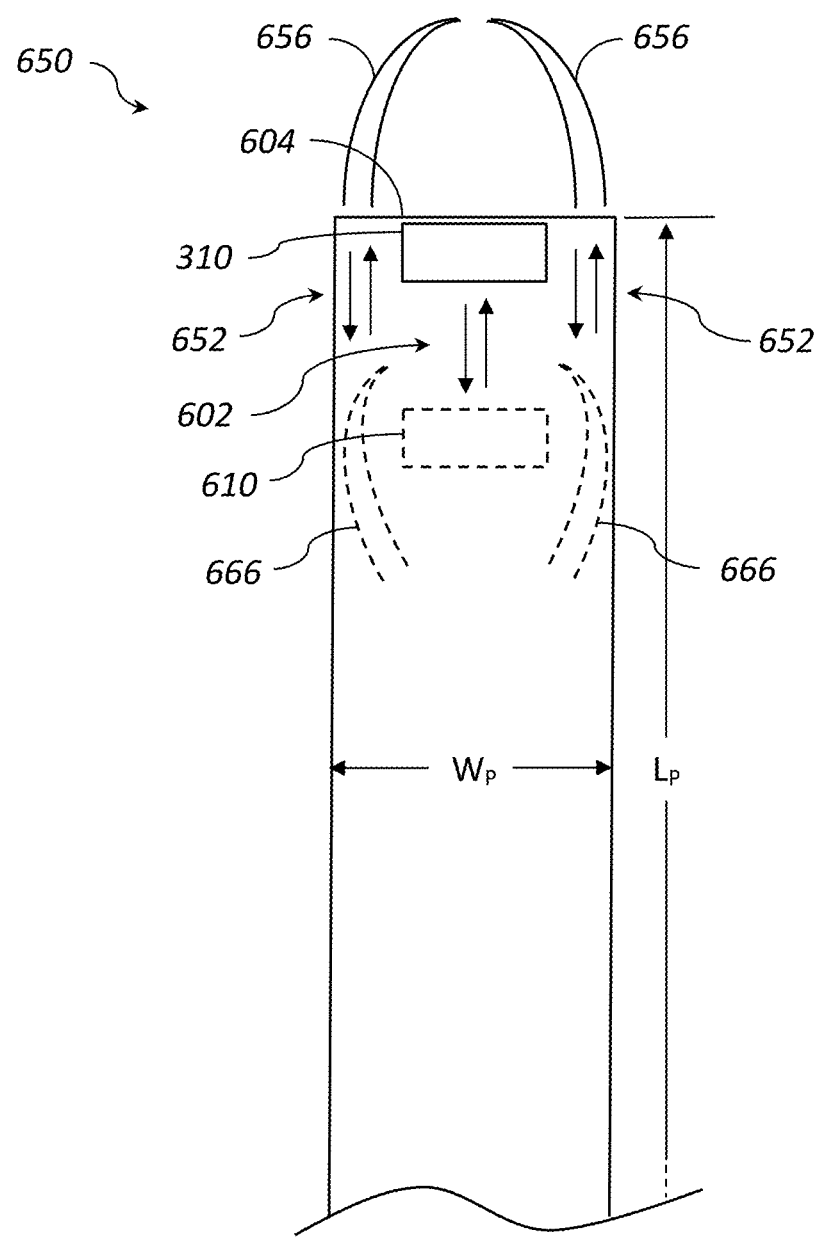
FIG. 6B shows another example embodiment of a tissue probe which includes a shield/piercing structure configured to be repositionable between an extended position (providing a barrier over the distal open end of the probe) and a retracted position; the tissue probe including a sample measuring device (optionally) configured to be repositionable between a forward/extended position adjacent the distal end (of the probe) and a rearward/retracted position recessed within the probe enclosure away from the distal open end.

FIG. 6B shows another example embodiment of a sample probe 650 (e.g., a tissue probe) configured with a sample measuring device 310, e.g., an attenuated total reflection infrared (ATR-IR) sample measuring device including a crystal defining a sample receiving surface/interface such as previously described in relation to FIG. 4. The sample probe 650 includes a distal open end 604 adjacent to which the sample measuring device 310 is located with its a sample receiving surface/interface distally directed (i.e., positioned and oriented in relation to the distal open end 604 to accommodate sample material advancing through the distal open end to be placed (pressed) against sample receiving surface/interface. In this example embodiment, the probe 650 includes surfaces/edges 656 configured (shaped) to provide a shield/piercing structure that is repositionable (as denoted by the bi-directional arrows 652) between forward/extended positions extended distally in relation to and providing a barrier over the distal open end 604 (of the probe) and rearward/retracted positions 666 (shown in dashed lines) recessed within the probe enclosure away the distal open end 604 (e.g., as shown). Optionally, in this embodiment, the sample measuring device 310 is configured to be repositionable (as denoted by the bi-directional arrows 602) between a forward/extended position adjacent the distal end (of the probe) and a rearward/retracted position 610 (shown in dashed lines) recessed within the probe enclosure away from the distal open end 604 (e.g., as shown).

In respect to repositionable components/componentry of the sample probes, various repositioning mechanisms can be utilized including manual, spring-biased, spring-based and/or actuator-driven elements, and potentially incorporating though on a smaller scale mechanisms analogous to the technologies employed with guarded surgical scalpels or surgical implements with extendable/retractable blades for example.

With reference to FIGS. 6A and 6B, the probes described herein have a probe length $L_P$ which can be variable 0-5 mm (typically around 1-2 mm), with a longest probe length $L_P$ of approx. 6 cm. The probes described herein have a probe width $W_P$ (or diameter) which can be approx. 1 mm or smaller so that the sample material (e.g., tissue) is not severely damaged during testing.

Figure 7:
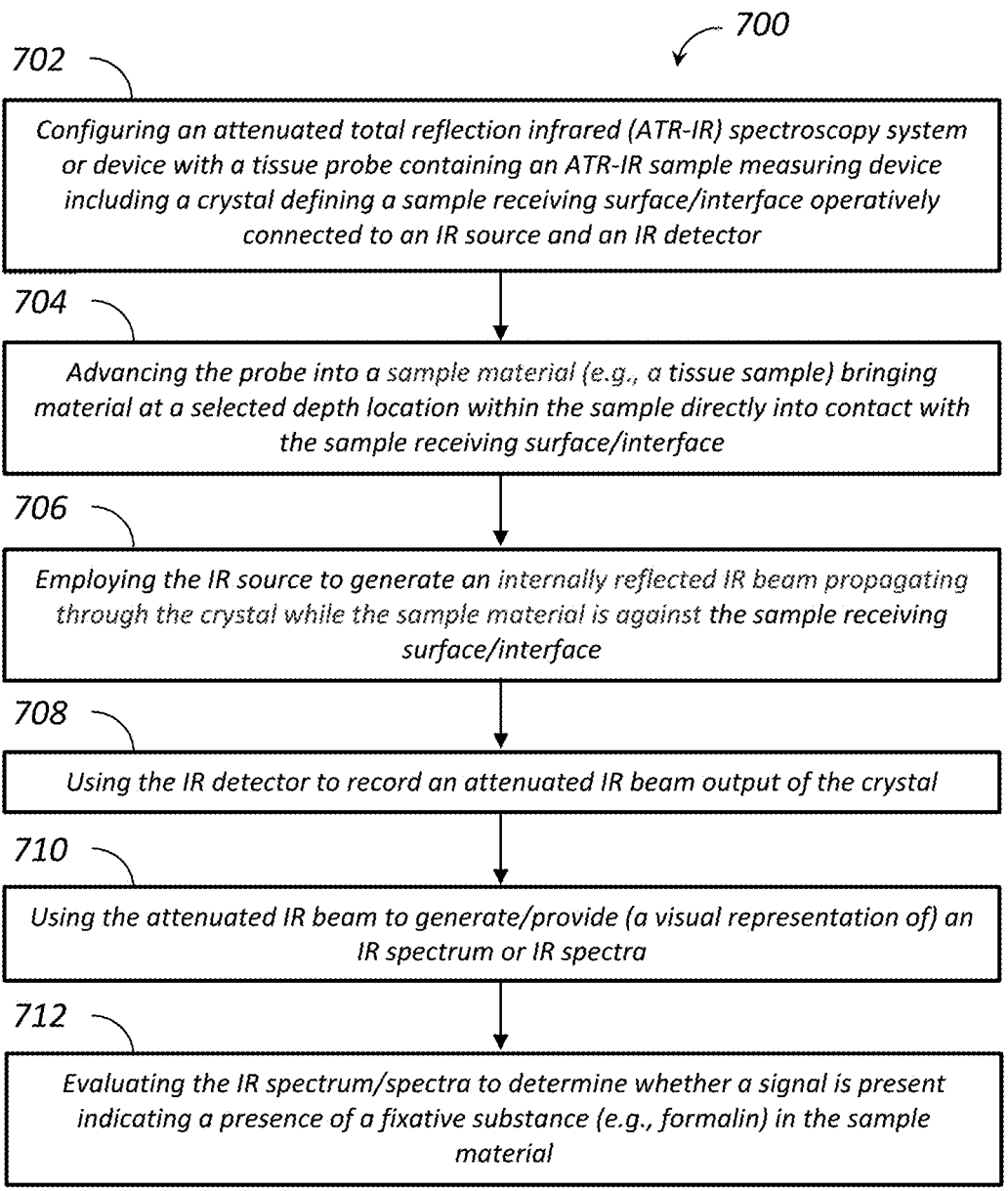
FIG. 7 is a flowchart showing steps of or associated with an example attenuated total reflection infrared (ATR-IR) sample (e.g., tissue sample) measuring methodology.

FIG. 7 is a flowchart showing steps of or associated with an example ATR-IR sample measuring method 700. At 702 (optional in some example methodologies), the method 700 includes configuring an spectroscopy system or device with a probe containing an ATR-IR sample measuring device including a crystal defining a sample receiving surface/interface operatively connected (e.g., optically coupled at opposite ends of the optical path of the crystal via associated optics) to an IR source and an IR detector. At 704, the method 700 includes advancing the probe into a sample material (e.g., a tissue sample) bringing material (tissue) at a selected depth location (denoted "L", FIG. 5) within the sample material directly into contact with the sample receiving surface/interface. Next at 706, the method 700 includes employing the IR source to generate an internally reflected IR beam propagating through the crystal while the material (e.g., tissue) at a selected depth location is against the sample receiving surface/interface. At 708, the method 700 includes using the IR detector to record an attenuated IR beam output of the crystal (as an interferogram signal). And at 710, the method 700 includes using the attenuated IR beam to generate/provide (a visual representation of) an IR spectrum or IR spectra. At 712 (optional in some example methodologies), the method 700 further includes evaluating the IR spectrum/spectra to determine whether a signal (e.g., a signal peak at approximately between 1000 cm$^{-1}$ and 1100 cm$^{-1}$) is present indicating a presence of a fixative substance (e.g., formalin) in the sample material at the selected depth location. In example methodologies, the sample material is a tissue sample. In example methodologies, the fixative substance is formalin/formaldehyde. In example methodologies, the selected depth location is approximately half the thickness of the sample material (or another depth location between the exterior/top surface of the sample and the location half way through the sample). The step 710 of using the attenuated IR beam to generate/provide an IR spectrum or IR spectra can include generating/providing a visual representation of spectra patterns respectively indicating measurement results obtained from measurements taken at different times. The step 710 of using the attenuated IR beam to generate/provide an IR spectrum or IR spectra can include generating/providing a visual representation of spectra patterns indicating measurement results obtained from measurements taken at different times and/or at different locations on or within the sample material. In example methodologies, the method 700 further includes, during (or after) grossing the sample material at an area of interest, obtaining measurements taken at different locations around or adjacent to the area of interest. For example, in the case of larger samples a pathologist/designee can visually examine the tissue sample and cut out areas of interest which will be processed for investigation (the process is called "grossing"). During grossing, the user can scan (assess) the areas immediately around the area of interest to determine extent of fixation and if the locations around the area of interest show presence of fixation then assume that the area of interest has also received its share (a sufficient amount) of the fixative. In example methodologies, the step 704 of advancing the probe into a sample material includes obtaining measurements taken at different locations around or adjacent to an area of interest of the sample material.

Example embodiments and implementations involve instrumentation configured or provided to facilitate such assessments of presence and intensity of fixative at (via) multiple different locations within a sample placement structure/area of a measuring instrument (e.g., for simultaneously measuring at the different locations). FIG. 3B shows an example of such a sample placement structure/area, namely, a sample placement structure 300-2 (e.g., a surface upon which a tissue sample to be measured is placed) that has a four (4) distinct spatially separated sample measuring devices 310 that each have a sample receiving surface/interface defined by a crystal such as for example an ATR-IR diamond. FIG. 3C shows another example of such a sample placement structure/area, namely, a sample placement structure 300-3 (e.g., a surface upon which a tissue sample to be measured is placed) that has a nine (9) distinct spatially separated sample measuring devices 310 that each have a sample receiving surface/interface defined by a crystal such as for example an ATR-IR diamond.

Figure 3D:
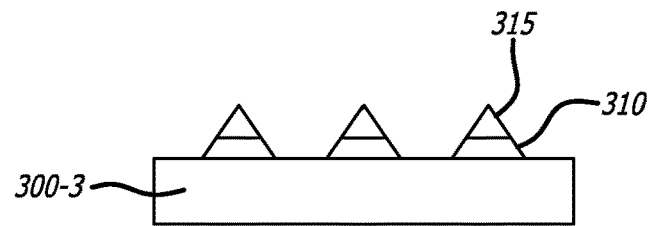
FIG. 3D shows a side view of the device of FIG. 3C and shows three sample measuring devices 310 each in a form of a raised piercing structure and each containing one or more ATR-IR sample measuring devices 315.

Example embodiments involve a spectroscopy system or device configured with a raised piercing structure containing multiple ATR-IR sample measuring devices provided on a sharp peak configured to penetrate into a sample material. A sample placement structure/area, having an spatial distribution of ATR-IR sample measuring devices such as shown in FIG. 3B or 3C for example, can be provided in the form of a raised piercing structure containing multiple ATR-IR sample measuring devices provided on a sharp peak configured to penetrate into a sample material. Alternatively, a sample placement structure/area can be provided in the form of a raised piercing structure containing multiple ATR-IR sample measuring devices each of which is provided on a separate (individual) sharp peak configured to penetrate into the sample material. Representatively, FIG. 3D shows a side view of the device of FIG. 3C and shows three sample measuring devices 310 each in a form of a raised piercing structure and each containing one or more ATR-IR sample measuring devices 315. Moreover, the sample placement structure/area and peaks or other piercing structures can be configured to penetrate to different depths within the sample material placed on the sample placement structure/area. In example embodiments, the multiple ATR-IR sample measuring devices include diamond crystals.

Figure 8:
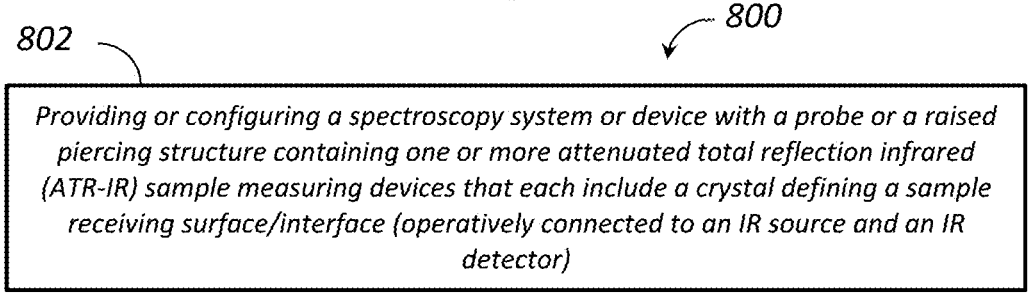
FIG. 8 is a flowchart showing an example method of instrumentation design.

FIG. 8 is a flowchart showing an example instrumentation design method 800. At 802, the method 800 includes providing or configuring a spectroscopy system or device with a probe or a raised piercing structure containing one or more attenuated total reflection infrared (ATR-IR) sample measuring devices that each include a crystal defining a sample receiving surface/interface (operatively connected to an IR source and an IR detector).

Thus, in an example embodiment, an instrumentation method includes providing or configuring a spectroscopy system or device with a probe or a raised piercing structure containing one or more attenuated total reflection infrared (ATR-IR) sample measuring devices which each include a crystal defining a sample receiving surface/interface.

Thus, in an example embodiment, an apparatus for measuring sample materials includes a spectroscopy system or device including or configured with a structure containing one or more attenuated total reflection infrared (ATR-IR) sample measuring devices that each include a crystal defining a sample receiving surface/interface. The sample receiving surface/interface of each of the ATR-IR sample measuring devices is operatively connected to an IR source and an IR detector. In example embodiments and implementations, the spectroscopy system or device includes a probe having a sample measuring device that is configured to be repositionable between a forward/extended position (adjacent a distal end of the probe) and a rearward/retracted position recessed within the probe enclosure away from the distal end. In example embodiments and implementations, the spectroscopy system or device includes a probe having a piercing structure and/or a cutter at a distal end of the probe. In example embodiments and implementations, the spectroscopy system or device includes a probe having a shield/piercing structure configured to be repositionable between an extended position, providing a barrier over a distal open end of the probe, and a retracted position. In example embodiments and implementations, the spectroscopy system or device includes a raised piercing structure containing multiple ATR-IR sample measuring devices provided on a sharp peak (of the structure) configured to penetrate into a sample material. By way of example, the multiple ATR-IR sample measuring devices include diamond crystals. In example embodiments and implementations, the one or more ATR-IR sample measuring devices include multiple ATR-IR sample measuring devices configured to measure a sample material at different depths respectively within the sample material. In example embodiments and implementations, the one or more ATR-IR sample measuring devices include multiple ATR-IR sample measuring devices configured to measure a sample material at different spatially separated locations respectively across the sample material. In example embodiments and implementations, the one or more ATR-IR sample measuring devices include multiple ATR-IR sample measuring devices configured to measure a sample material at different spatially separated locations respectively across the sample material. In example embodiments and implementations, the spectroscopy system or device includes a probe with a sample placement structure/area containing multiple ATR-IR sample measuring devices. In example embodiments and implementations, the spectroscopy system or device includes a raised piercing structure with a sample placement structure/area containing multiple ATR-IR sample measuring devices.

Figure 9:
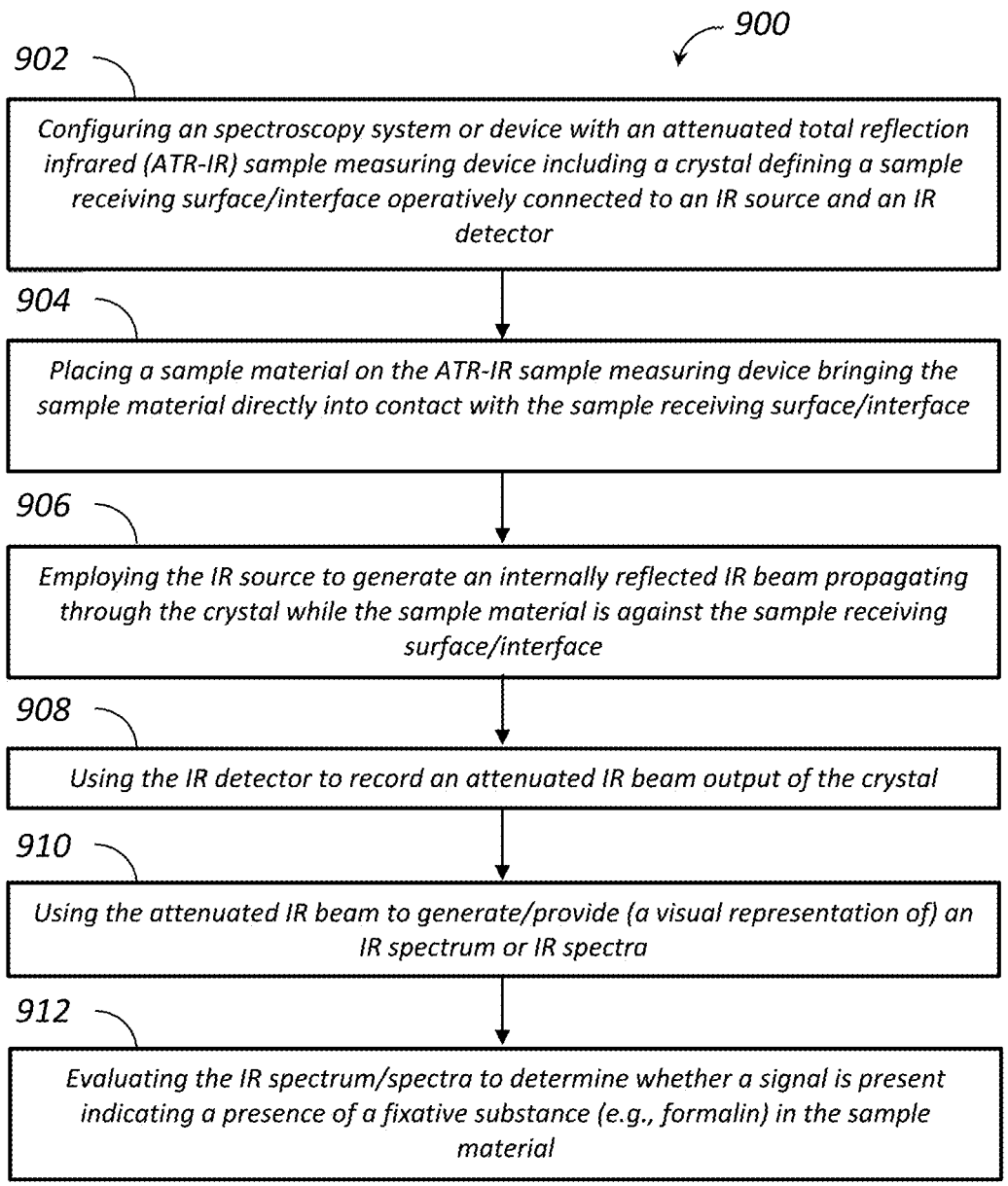
FIG. 9 is a flowchart showing steps of or associated with an example attenuated total reflection infrared (ATR-IR) sample (e.g., tissue sample) measuring methodology which does not involve (or require) using a probe to penetrate a sample material.

FIG. 9 is a flowchart showing steps of or associated with an example ATR-IR sample measuring method 900 which does not involve (or require) using a probe to penetrate a sample material. At 902 (optional in some example methodologies), the method 900 includes configuring an spectroscopy system or device with an ATR-IR sample measuring device including a crystal defining a sample receiving surface/interface operatively connected (e.g., optically coupled at opposite ends of the optical path of the crystal via associated optics) to an IR source and an IR detector. At 904, the method 900 includes placing a sample material (e.g., a tissue sample) on the ATR-IR sample measuring device bringing the sample material (e.g., a tissue sample) directly into contact with the sample receiving surface/interface. Next at 906, the method 900 includes employing the IR source to generate an internally reflected IR beam propagating through the crystal while the sample material (e.g., tissue) is against the sample receiving surface/interface. At 908, the method 900 includes using the IR detector to record an attenuated IR beam output of the crystal (as an interferogram signal). And at 910, the method 900 includes using the attenuated IR beam to generate/provide (a visual representation of) an IR spectrum or IR spectra. At 912 (optional in some example methodologies), the method 900 further includes evaluating the IR spectrum/spectra to determine whether a signal (e.g., a peak at approximately between 1000 cm-1 and 1100 cm-1) is present indicating a presence of a fixative substance (e.g., formalin) in the sample material. In example methodologies, the sample material is a tissue sample. In example methodologies, the fixative substance is formalin/formaldehyde. In example methodologies, the method 900 further includes, prior to placing the sample material, grossing the sample material to expose material at a selected depth location within the sample material, and the step 904 of placing a sample material includes placing the sample material on the ATR-IR sample measuring device bringing exposed material at the selected depth location directly into contact with the sample receiving surface/interface. In example methodologies, the selected depth location is approximately half the thickness of the sample material (or another depth location between the exterior/top surface of the sample and the location half way through the sample). In example methodologies, the method 900 further includes, after grossing the sample material and prior to placing the sample material, washing and removing excess fluid on the sample material including the exposed material at the selected depth location. The step 910 of using the attenuated IR beam to generate/provide an IR spectrum or IR spectra can include generating/providing a visual representation of spectra patterns respectively indicating measurement results obtained from measurements taken at different times. The step 910 of using the attenuated IR beam to generate/provide an IR spectrum or IR spectra can include generating/providing a visual representation of spectra patterns indicating measurement results obtained from measurements taken at different times and/or at different locations on or exposed surfaces of the sample material. In example methodologies, the method 900 further includes, during (or after) grossing the sample material at an area of interest, obtaining measurements taken at different locations around or adjacent to the area of interest. For example, in the case of larger samples a pathologist/designee can visually examine the tissue sample and cut out areas of interest which will be processed for investigation (the process is called "grossing"). During grossing, the user can scan (assess) the areas immediately around the area of interest to determine extent of fixation and if the locations around the area of interest show presence of fixation then assume that the area of interest has also received its share (a sufficient amount) of the fixative. In example methodologies, the step 904 of placing a sample material on the ATR-IR sample measuring device includes obtaining measurements taken at different locations around or adjacent to an area of interest of the sample material.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a processor or application specific processor.

Unless specifically stated otherwise, it may be appreciated that terms such as "processing," "computing," "calculating," "determining," or the like, refer to the action and/or processes of a computer or computing system, or similar electronic computing device, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by hardware as discussed above, as an alternative the same may also be embodied in dedicated hardware or a combination of software/hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc.

The flow charts and methods described herein show the functionality and operation of various implementations. If embodied in software, each block, step, or action may represent a module, segment, or portion of code that comprises program instructions to implement the specified logical functions. The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical functions.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as described herein.

What is claimed is:

1. An attenuated total reflection infrared (ATR-IR) sample material measuring method comprising:
   configuring an spectroscopy system or device with a probe containing an ATR-IR sample measuring device including a crystal defining a sample receiving surface/interface operatively connected to an IR source and an IR detector;
   advancing the probe into a sample material bringing material at a selected depth location directly into contact with the sample receiving surface/interface;
   employing the IR source to generate an internally reflected IR beam propagating through the crystal while the material at a selected depth location is against the sample receiving surface/interface;
   using the IR detector to record an attenuated IR beam output of the crystal;
   using the attenuated IR beam to generate/provide an IR spectrum or IR spectra; and
   evaluating the IR spectrum/spectra to determine whether a signal is present indicating a presence of a fixative substance in the sample material at the selected depth location.

2. The attenuated total reflection infrared (ATR-IR) sample material measuring method of claim 1, wherein the fixative substance is formaldehyde.

3. The attenuated total reflection infrared (ATR-IR) sample material measuring method of claim 1, wherein the sample material is a tissue sample.

4. The attenuated total reflection infrared (ATR-IR) sample material measuring method of claim 1, wherein the step of advancing the probe into a sample material includes obtaining measurements taken at different locations around or adjacent to an area of interest of the sample material.

5. The attenuated total reflection infrared (ATR-IR) sample material measuring method of claim 1, wherein the selected depth location is approximately half the thickness of the sample material.

6. The attenuated total reflection infrared (ATR-IR) sample material measuring method of claim 1, wherein the step of using the attenuated IR beam to generate/provide an IR spectrum or IR spectra includes generating/providing a visual representation of spectra patterns respectively indicating measurement results obtained from measurements taken at different times.

7. The attenuated total reflection infrared (ATR-IR) sample material measuring method of claim 1, wherein the step of using the attenuated IR beam to generate/provide an IR spectrum or IR spectra includes generating/providing a visual representation of spectra patterns indicating measurement results obtained from measurements taken at different times and/or at different locations on or within the sample material.

8. An apparatus for measuring sample materials comprising:
a spectroscopy system or device comprising a probe comprising an attenuated total reflection infrared (ATR-IR) sample measuring device comprising a crystal defining a sample receiving surface/interface, wherein the sample measuring device is configured to be repositionable between a forward/extended position adjacent a distal end of the probe and a rearward/retracted position recessed within the probe enclosure away from the distal end.

9. The apparatus for measuring sample materials of claim 8, wherein the sample receiving surface/interface of the ATR-IR sample measuring device is operatively connected to an IR source and an IR detector.

10. The apparatus for measuring sample materials of claim 8, wherein the probe comprises a piercing structure and/or a cutter at a distal end of the probe.

11. The apparatus for measuring sample materials of claim 8, wherein the probe comprises a shield/piercing structure configured to be repositionable between an extended position, providing a barrier over a distal open end of the probe, and a retracted position.

12. The apparatus for measuring sample materials of claim 8, wherein the crystal comprises a diamond crystal.

13. The apparatus for measuring sample materials of claim 8, wherein probe comprises a sample placement structure/area containing multiple ATR-IR sample measuring devices.

14. An attenuated total reflection infrared (ATR-IR) sample material measuring method comprising:
configuring an spectroscopy system or device with an ATR-IR sample measuring device including a crystal defining a sample receiving surface/interface operatively connected to an IR source and an IR detector;
placing a sample material on the ATR-IR sample measuring device bringing the sample material directly into contact with the sample receiving surface/interface;
employing the IR source to generate an internally reflected IR beam propagating through the crystal while the sample material is against the sample receiving surface/interface;
using the IR detector to record an attenuated IR beam output of the crystal;
using the attenuated IR beam to generate/provide an IR spectrum or IR spectra; and
evaluating the IR spectrum/spectra to determine whether a signal is present indicating a presence of a fixative substance in the sample material.

15. The attenuated total reflection infrared (ATR-IR) sample material measuring method of claim 14, wherein the fixative substance is formaldehyde.

16. The attenuated total reflection infrared (ATR-IR) sample material measuring method of claim 14, wherein the sample material is a tissue sample.

17. The attenuated total reflection infrared (ATR-IR) sample material measuring method of claim 14, wherein the step of placing a sample material on the ATR-IR sample measuring device includes obtaining measurements taken at different locations around or adjacent to an area of interest of the sample material.

18. The attenuated total reflection infrared (ATR-IR) sample material measuring method of claim 14, further comprising:
prior to placing the sample material, grossing the sample material to expose material at a selected depth location within the sample material; and
wherein the step of placing a sample material comprises placing the sample material on the ATR-IR sample measuring device bringing exposed material at the selected depth location directly into contact with the sample receiving surface/interface.

19. The attenuated total reflection infrared (ATR-IR) sample material measuring method of claim 18, wherein the selected depth location is approximately half the thickness of the sample material.

20. The attenuated total reflection infrared (ATR-IR) sample material measuring method of claim 18, further comprising:
after grossing the sample material and prior to placing the sample material, washing and removing excess fluid on the sample material including the exposed material at the selected depth location.

21. The attenuated total reflection infrared (ATR-IR) sample material measuring method of claim 14, wherein the step of using the attenuated IR beam to generate/provide an IR spectrum or IR spectra includes generating/providing a visual representation of spectra patterns respectively indicating measurement results obtained from measurements taken at different times.

22. The attenuated total reflection infrared (ATR-IR) sample material measuring method of claim 14, wherein the step of using the attenuated IR beam to generate/provide an IR spectrum or IR spectra includes generating/providing a visual representation of spectra patterns indicating measurement results obtained from measurements taken at different times and/or at different locations on or exposed surfaces of the sample material.

* * * * *